US008861305B2

(12) United States Patent
Nakabayashi

(10) Patent No.: US 8,861,305 B2
(45) Date of Patent: Oct. 14, 2014

(54) ACOUSTIC WAVE ACQUIRING APPARATUS AND CONTROL METHOD THEREOF

(75) Inventor: Takaaki Nakabayashi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 144 days.

(21) Appl. No.: 13/616,110

(22) Filed: Sep. 14, 2012

(65) Prior Publication Data

US 2013/0094327 A1    Apr. 18, 2013

(30) Foreign Application Priority Data

Oct. 18, 2011   (JP) .................................. 2011-228945

(51) Int. Cl.
| | | |
|---|---|---|
| *G01S 15/89* | (2006.01) | |
| *A61B 8/00* | (2006.01) | |
| *A61B 5/00* | (2006.01) | |
| *G01S 7/52* | (2006.01) | |

(52) U.S. Cl.
CPC ........... *A61B 5/0095* (2013.01); *G01S 15/8938* (2013.01); *A61B 8/4209* (2013.01); *G01S 15/899* (2013.01); *G01S 7/52079* (2013.01)
USPC ........................................................... 367/7

(58) Field of Classification Search
CPC   A61B 8/4209;  A61B 5/0095;  G01S 15/8938;
                                 G01S 7/52079;  G01S 15/899
USPC ................................... 367/7, 11, 87; 600/445
See application file for complete search history.

(56) References Cited

U.S. PATENT DOCUMENTS

| | | | |
|---|---|---|---|
| 2010/0026787 A1* | 2/2010 | Yasuda et al. .................... 348/47 |
| 2012/0330163 A1 | 12/2012 | Nakabayashi ................ 600/476 |
| 2013/0094327 A1* | 4/2013 | Nakabayashi ................... 367/87 |
| 2013/0239687 A1* | 9/2013 | Nakabayashi .................. 73/574 |

FOREIGN PATENT DOCUMENTS

| | | | |
|---|---|---|---|
| JP | 2011-103913 | | 6/2011 |
| JP | 2013085705 A | * | 5/2013 |
| WO | WO 99/049504 A | | 9/1999 |
| WO | WO 2011/058724 A | | 5/2011 |
| WO | WO 2011/132412 | | 10/2011 |

\* cited by examiner

*Primary Examiner* — Daniel Pihulic
(74) *Attorney, Agent, or Firm* — Fitzpatrick, Cella, Harper & Scinto

(57) ABSTRACT

The present invention provides an acoustic wave acquiring apparatus including: a probe configured to receive an acoustic wave from an object through an object holding unit that holds the object; an acoustic matching material holding unit configured to form a space, which holds an acoustic matching material, between the object holding unit and the probe; a scanning unit configured to allow the probe to scan in a first direction on the surface of the object holding unit, and in a second direction crossing the first direction; and a supplying unit configured to supply the acoustic matching material to the space by using a predetermined supply-amount pattern, wherein the supplying unit uses different supply-amount patterns in the case where the probe scans in the first direction and in the case where the probe scans in the second direction.

10 Claims, 12 Drawing Sheets

ACOUSTIC WAVE ACQUIRING APPARATUS AND CONTROL METHOD THEREOF

BACKGROUND OF THE INVENTION

1. Field of the Invention

The present invention relates to an acoustic wave acquiring apparatus and control method thereof.

2. Description of the Related Art

There has been known an ultrasound apparatus (acoustic wave acquiring apparatus) as an apparatus for acquiring image information of an object. As the ultrasound apparatus described above, Japanese Patent Application Laid-Open No. 2011-103913 (Patent Literature 1: PTL 1) describes an apparatus configured to hold and press the object by two opposing holding plates, and to two-dimensionally scan a probe in a horizontal direction and in a vertical direction in order to acquire an image. In the ultrasound apparatus described above, matching oil is filled between the probe and the holding plate in order to realize an acoustic impedance matching between the probe and the holding plate. The matching oil is retained by an oil seal arranged to enclose the probe. The oil seal has an opening formed on its top surface from which air bubbles mixed in the matching oil can be removed.

International Publication No. WO99/049504 (Patent Literature 2: PTL 2) describes a technique of filling liquid between a member that is mechanically scanned and a fixed member in order to prevent air from entering. The apparatus described in PTL 2 is a projection exposure apparatus including a two-dimensional scanning stage that can realize two-axis scan in the horizontal direction, and a projection optical system that projects light onto a wafer provided on a stage from above. This apparatus is also provided with a liquid supplying apparatus for filling liquid between the surface of the wafer and the bottom surface of the projection optical system, wherein the liquid is supplied between the surface of the wafer and the bottom surface of the projection optical system from a liquid supplying nozzle and a liquid collecting nozzle. When the wafer moves, the supplied liquid goes out, and air might enter. To deal with the problem, the liquid is continuously supplied at all times. Since the position where air enters is different depending upon the moving direction of the wafer, plural supplying nozzles and plural collecting nozzles are provided at each positions corresponding to the moving direction of the wafer. The liquid is supplied from the nozzle corresponding to the moving direction of the wafer out of the plural supplying nozzles. The liquid supplying apparatus has a control unit for a supply amount of the liquid. The supply amount of each of the supplying nozzles on the corresponding positions is adjusted according to the moving speed of the wafer.

PTL 1: Japanese Patent Application Laid-Open No. 2011-103913

PTL 2: International Publication No. WO99/049504

SUMMARY OF THE INVENTION

In PTL 1, the supply amount of the matching oil of the ultrasound apparatus is constant, regardless of the scanning speed. A tilt occurs on a liquid level of the matching oil due to the acceleration exerted during the acceleration until the probe reaches the scanning speed from its stopped state, or the acceleration exerted during the deceleration until the probe moving with the scanning speed stops. The liquid level lowers due to the tilt on the liquid level, so that air might enter between the probe and the holding plate. The higher the acceleration becomes, the larger the amount of the decrease on the liquid level becomes.

A flow occurs on the matching oil in the vicinity of the holding plate due to the fluid friction with the holding plate. Therefore, even when the probe scans with a constant speed, the liquid level lowers. This phenomenon also allows air to enter between the probe and the holding plate. The amount of the decrease of the liquid level increases, as the speed increases. However, PTL 1 does not describe in detail the supply amount of oil in the ultrasound apparatus. Therefore, the oil might be excessively supplied depending upon the scanning direction or scanning condition, resulting in that a lot of oil might leak from an opening.

In the liquid supplying apparatus described in PTL 2, there is only one pattern for changing the supply amount of the liquid according to the change in the speed for one supplying nozzle. Therefore, when the supply amount is changed by using only one supplying port, a condition for a large decrease amount of the liquid surface has to be set. Accordingly, the matching oil might be supplied more than necessary depending upon the scanning direction or the scanning condition such as acceleration or constant speed moving. As a result the amount of the matching oil leaking from the opening on the top surface of a seal member might increase. This entails a problem that a large amount of matching oil might scatter in the apparatus. The scattering matching oil contaminates the inside of the apparatus. As the scattering amount is large, the decrease amount of oil in the oil tank is large.

The oil has to be replenished by the decreased amount, which is uneconomical.

The present invention is accomplished in view of the foregoing problem, and the objection of this invention is to appropriately control a supply amount of an acoustic matching material with a scan of a probe.

The present invention provides an acoustic wave acquiring apparatus comprising:

a probe configured to receive an acoustic wave from an object via an object holding unit that holds the object;

an acoustic matching material holding unit configured to form a space, which holds an acoustic matching material, between the object holding unit and the probe;

a scanning unit configured to allow the probe to scan in a first direction on the surface of the object holding unit, and in a second direction crossing the first direction; and a supplying unit configured to supply the acoustic matching material to the space by using a predetermined supply-amount pattern, wherein the supplying unit uses different supply-amount patterns in the case where the probe scans in the first direction and in the case where the probe scans in the second direction.

The present invention also provides a control method of an acoustic wave acquiring apparatus including a probe that receives an acoustic wave from an object via an object holding unit that holds the object, and an acoustic matching material holding unit that forms a space, which holds an acoustic matching material, between the object holding unit and the probe, the method comprising:

a scanning step in which a scanning unit allows the probe to scan in a first direction on the surface of the object holding unit, and in a second direction crossing the first direction; and a supplying step in which a supplying unit supplies the acoustic matching material to the space by using a predetermined supply-amount pattern, wherein different supply-amount patterns are used in the case where the probe scans in the first direction and in the case where the probe scans in the second direction, in the supplying step.

The present invention can appropriately control a supply amount of an acoustic matching material with a scan of a probe.

Further features of the present invention will become apparent from the following description of exemplary embodiments with reference to the attached drawings.

DESCRIPTION OF THE EMBODIMENTS

Preferable embodiments of the present invention will be described below with reference to the drawings. The size, material, shape, and their relative arrangement of components described herein should appropriately be changed depending upon a configuration to which the present invention is applied, and various conditions, and are not intended to limit the scope of the present invention.

In the embodiments described below, a photoacoustic apparatus that scans an object, such as a human body, by using a probe will be described as one example. In the photoacoustic apparatus, when light is irradiated to the object, an acoustic wave (typically, an ultrasound wave) is generated from the object by photoacoustic effect. The acoustic wave includes an elastic wave called sonic wave or ultrasound wave. The acoustic wave generated by the photoacoustic effect is called photoacoustic ultrasound wave. The present invention is applied to a probe including a receiving element that receives an acoustic wave and converts the acoustic wave into an electric signal. The photoacoustic apparatus acquires characteristic information such as an initial acoustic distribution in the object, or optical absorption coefficient distribution or substance concentration distribution based upon the initial acoustic distribution from the converted electric signal, and forms an image of the inside of the object. The photoacoustic apparatus described above is also referred to as an acoustic wave acquiring apparatus that receives an acoustic wave by use of a probe.

Therefore, the present invention is also applicable to another acoustic wave acquiring apparatus using a probe. For example, the present invention is applicable to an acoustic wave acquiring apparatus (ultrasound apparatus) that receives an echo wave, which is transmitted to the object from the probe and reflected in the object, and constructs an image of the inside of the object.

<Embodiment 1>

Figure 1:
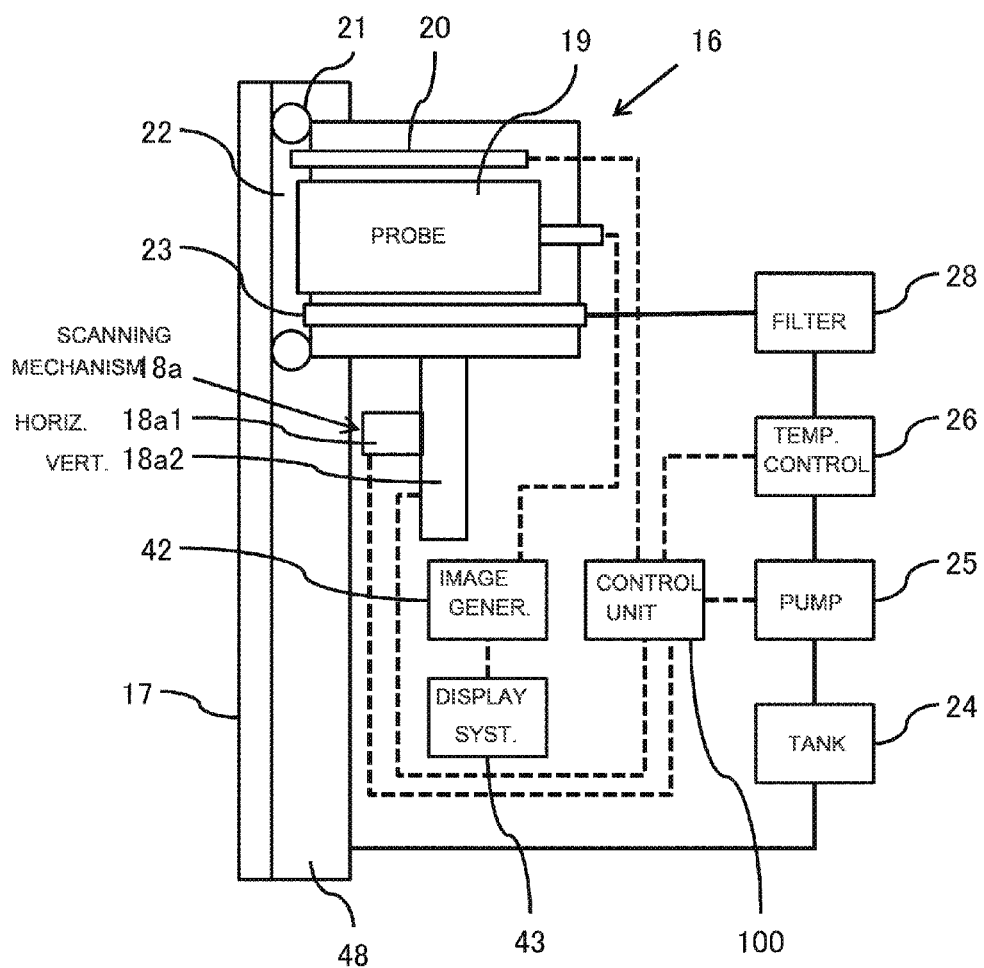
FIG. 1 is a view illustrating a schematic configuration of a photoacoustic apparatus according to an embodiment 1.
Figure 2:
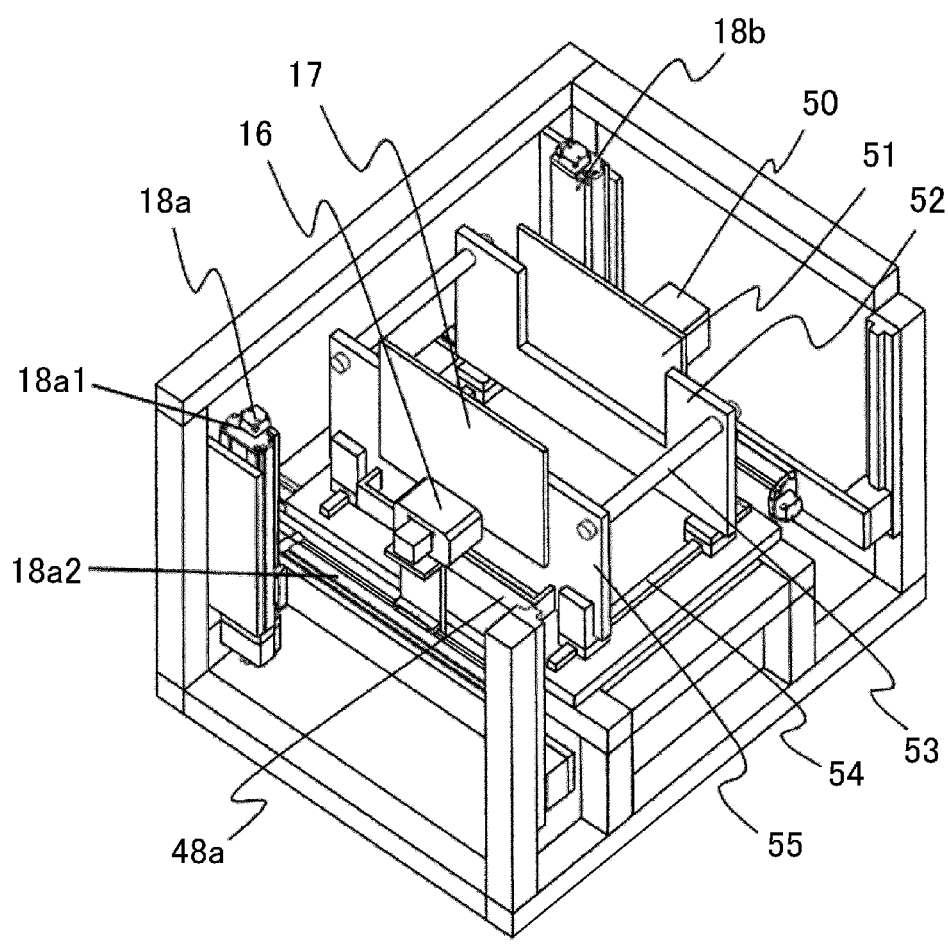
FIG. 2 is a perspective view of the photoacoustic apparatus according to the embodiment.

FIG. 1 is a view illustrating a configuration of a photoacoustic apparatus that is an example of an acoustic wave acquiring apparatus according to the present embodiment, and FIG. 2 is a perspective view of the photoacoustic apparatus.

A probe unit 16 is arranged on a two-axis probe scanning unit 18a that includes a horizontal scanning mechanism 18a1 that makes a scan in the horizontal direction, and a vertical scanning mechanism 18a2 that makes a scan in the vertical direction. The probe unit 16 can make a two-dimensional scan along a surface of a fixed holding plate 17. The holding plate 17 is a plate on which the probe makes a scan on its surface, and it corresponds to an object holding unit according to the present invention. The probe scanning unit 18a corresponds to a scanning unit according to the present invention. The horizontal direction corresponds to a first direction in the present invention, and the vertical direction crossing the horizontal direction corresponds to a second direction in the present invention. An object to be measured is pressed and held by the holding plate 17 and a movable holding plate 51 opposite to the holding plate 17. The holding plate 17 is fixed to a fixed plate 55, while the movable holding plate 51 is fixed to a movable plate 52. The fixed plate 55 and the movable plate 52 are provided so as to be capable of moving parallel by a guide rod 53 and a linear guide 54. A measured region of the object is put between the holding plate 17 and the holding plate 51, and the space between the holding plate 17 and the movable holding plate 51 is controlled by a pressing mechanism not illustrated, such as a mechanism using a trapezoidal thread and a bevel gear, or an air cylinder mechanism, in order to hold the object. An optical system 50 for irradiating light to the object is arranged on a position opposite to the probe unit 16 across the holding plate 17 and the movable holding plate 51. The optical system 50 can make a two-dimensional scan by a two-axis optical scanning unit 18b including an axis in the horizontal direction and an axis in the vertical direction like the probe scanning unit 18a. The probe scanning unit 18a and the optical scanning unit 18b may be configured by a motor, a ball screw, and a guide, may be configured by a motor, a gear, and a belt link, or may be configured by an air cylinder and a guide. A light source 50 and the probe unit 16 arranged to be opposite to each other across the object can always be scanned on the opposite position by synchronously controlling the probe scanning unit 18a and the optical scanning unit 18b.

Figure 3:
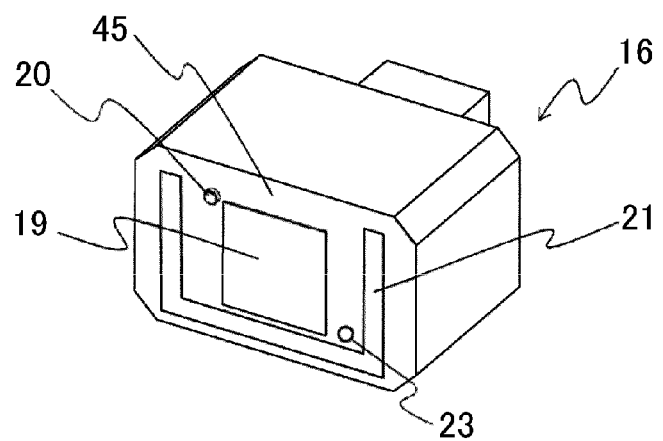
FIG. 3 is a perspective view of a probe unit.

FIG. 3 is a perspective view of the probe unit 16.

The probe unit 16 includes a probe 19 that measures an ultrasound wave generated from the object via the holding plate 17. The material of the holding plate 17 is preferably resin in order to realize the acoustic impedance matching from the object to the probe 19. Polymethylpentene is more preferably used. The probe unit 16 has a seal member 21 that encloses the probe 19. A gasket made of a material such as rubber, porous material (sponge), leather, or resin can be used as the seal member 21. The seal member 21 forms a space 22 into which matching oil for realizing the acoustic impedance matching between the holding plate 17 and the probe 19 is retained (see also FIG. 1). The seal member 21 corresponds to an acoustic matching material holding unit in the present invention. An opening 45 is formed on the top of the seal member 21 for allowing air mixed in the matching oil to escape. The probe unit 16 is provided with a supply port 23 for supplying the matching oil into the space 22. The matching oil stored in a tank 24 is supplied via a pipe 29 by a pump 25 serving as a supplying unit. Degassed matching oil is preferably used. The system for supplying the matching oil corresponds to a supplying unit in the present invention. In the present embodiment, the matching oil is used as the acoustic matching material for realizing the acoustic impedance matching. Therefore, the matching oil will be described below. Note that not only the matching oil such as ricinus, but also water or acoustic gel can be used as the acoustic matching material.

The tank 24 and the pipe 29 not illustrated can be made of polyethylene or stainless. However, it is preferable to provide an earth wire to the tank made of stainless for grounding, since the tank made of stainless is sometimes electrostatically charged when the insulating matching oil is circulated. The tank 24 is provided with a liquid-level monitoring unit, not illustrated, which senses the decrease of the matching oil due to an abnormal leakage. The unit for monitoring the liquid level may be a system by which the matching oil can be sensed even if the matching oil is insulating, such as a flow system, an optical system, or an ultrasound system.

As illustrated in FIG. 1, the matching oil sent from the tank 24 is supplied by a drive of the pump 25 to the space 22 from the supply port 23 via a temperature control system 26 and a filter 28. The temperature control system 26 has a function of measuring the temperature of the sent matching oil and a function of heating or cooling the matching oil in order to adjust the temperature of the matching oil to a predetermined temperature. With this, the variation in the temperature condition of the matching oil or the probe 19 is suppressed, so that the stable measurement can be realized. The filter 28 has a function of eliminating dusts in order to prevent the dusts mixed in the matching oil during the circulation from entering the space 22. For example, a mesh filter can be used. This structure can prevent the generation of measurement noise, or damage on the probe 19 and the holding plate 17, due to the dusts.

The space 22 (at least the portion between the holding plate 17 and the probe 19) formed by the holding plate 17, the probe 19, and the seal member 21 is filled with the matching oil during the measurement. A liquid-level sensor 20 is mounted above the probe 19 in the probe unit 16. When the liquid-level sensor 20 senses the matching oil, it can be determined that the matching oil is filled between the holding plate 17 and the probe 19.

A collecting system 48 serving as a collecting unit for collecting the matching oil leaked to the outside of the space 22 from the seal member 21 is mounted below the holding plate 17. The collecting system 48 includes a receiving container 48a (see FIG. 2) receiving the matching oil dripping through the holding plate 17, and a pipe connecting the receiving container 48a and the tank 24. The matching oil leaked out of the seal member 21 is collected in the collecting system 48, and circulated in the tank 24, during the measurement. The shape and the volume of the space 22 is designed such that, even when the matching oil is leaked with the movement of the probe unit 16, the matching oil sufficiently filling the portion between the holding plate 17 and the probe 19 is left from the start of the measurement till the end of the measurement.

The measurement and a control method according to the apparatus of the present embodiment will be described next.

The process described below is executed by the control unit 100 in FIG. 1. The control unit 100 is configured by a microcontroller or a computer, and it is a control system for controlling drive units 18a and 18b, the pump 25, and the temperature control system 26. The result sensed by the matching oil monitoring unit and the information such as the temperature of the matching oil measured by the temperature control system 26 are inputted to the control unit 100, and utilized for the supply of the matching oil and the temperature control.

As a preparation before the measurement, the control unit 100 confirms whether or not the matching oil is filled in the space 22 based upon the result sensed by the matching oil monitoring unit. If it is confirmed that the matching oil is filled in the space 22, the preparation before the measurement is completed. If it is confirmed that the matching oil is not filled in the space 22, the control unit 100 drives the pump 25 so as to supply the matching oil into the space 22. Thereafter, when the control unit 100 senses that the matching oil is filled in the space 22 from the result sensed by the matching oil monitoring unit, the control unit 100 stops the pump 25. With the preparation before the measurement described above, the space 22 between the holding plate 17 and the probe 19 can be filled with the matching oil in an appropriate amount, whereby the preparation for performing a satisfactory measurement is done. The pump 25 is driven according to the speed in the horizontal scan or the speed in the vertical scan, described later, during the measurement.

Figure 4:
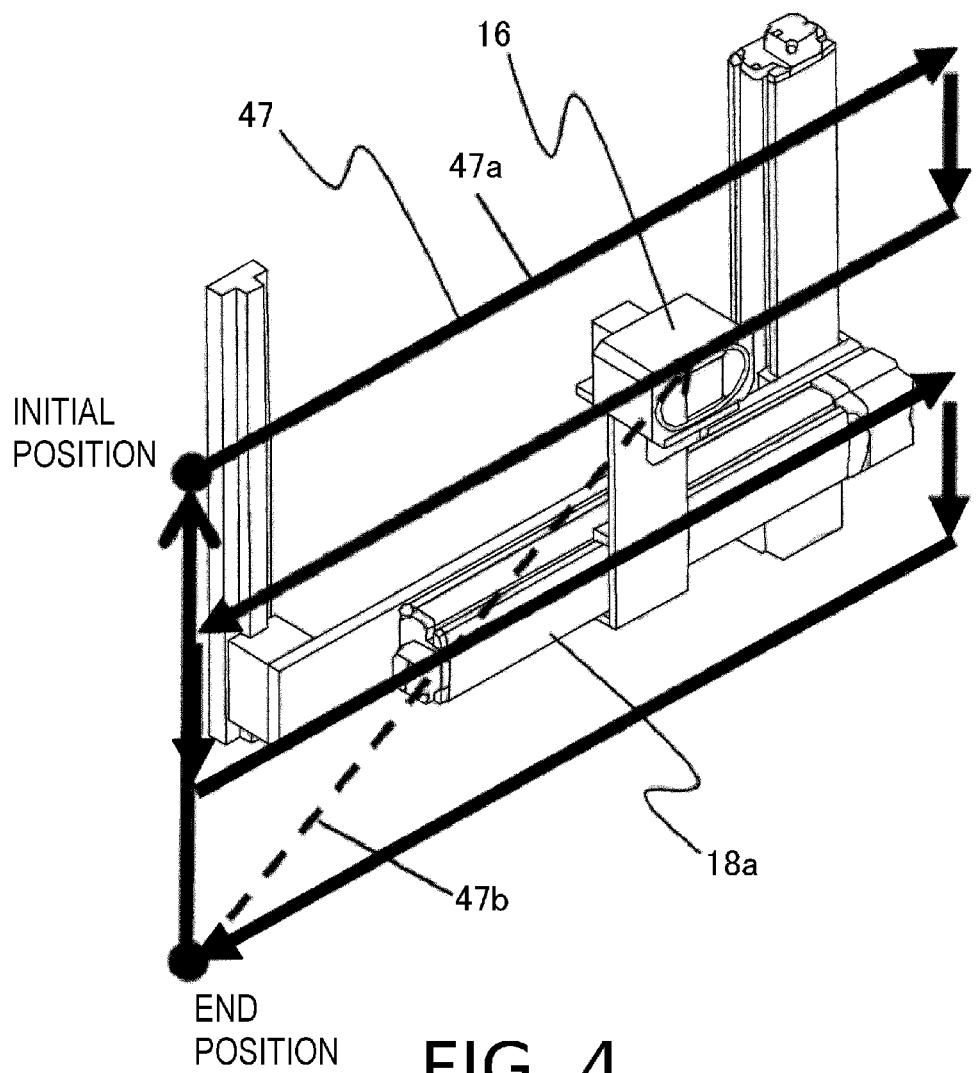
FIG. 4 is a view illustrating one example of a driving method of the probe unit during a measurement.

FIG. 4 is a view illustrating a trajectory of the probe unit 16 during the measurement. An arrow 47 indicates a trajectory of the movement of the probe unit 16 during the measurement. At an initial stage in the measurement, the probe unit 16 is located on the uppermost side end of the measurement range. When the measurement is started, the probe unit 16 scans in a horizontal direction to make a scan for 1 line, and then, moves to the next line below and scans in the reverse direction in the horizontal direction to make a scan for the next line below, as indicated by the arrow 47. The probe unit 16 repeats this operation, thereby making a scan one line by one line from the head. When the probe unit 16 reaches the end position, it returns to the initial position. When air bubbles are mixed in the matching oil in the space 22, the air bubbles can be released from the opening 45 during when the probe unit 16 is driven from top down. The scanning method is not limited to the line-by-line scan described above. For example, a method in which the probe is directly moved to a position to be measured as indicated by an arrow 47b in FIG. 4, and measures with the probe unit 16 being stopped, or a step-and-repeat method in which the probe unit 16 repeatedly moves and stops, and makes a measurement during when it stops, can be employed.

The probe 19 converts the received acoustic wave into an electric signal, and outputs the resultant to an image generating unit 42. The image generating unit 42 generates an image indicating information of the inside of the living body based upon the signal. Various reconstruction techniques conventionally known can be used as the technique of constructing the information of the inside of the living body from the acoustic wave signal. The image gene rated by the image generating unit 42 is outputted to a display system 43.

The liquid level of the matching oil upon the horizontal scan of the probe unit 16 will be described next.

Figure 5:
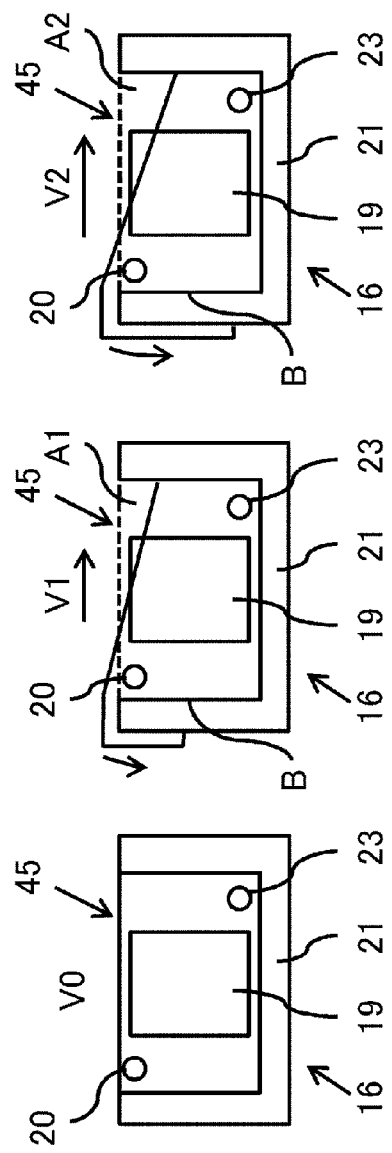
FIGS. 5A to 5C are views illustrating a state of a liquid level during a horizontal scan.

FIG. 5 is a schematic view illustrating the state of the liquid level of the matching oil, when the probe unit 16 scans in the horizontal direction in a state in which the matching oil is filled in the space 22, and then, the matching oil is not supplied. FIG. 5A illustrates a state in which the probe unit 16 stops. FIG. 5B illustrates a state in which the probe unit 16 scans with a constant speed (V1). FIG. 5C illustrates a state in which the probe unit 16 scans with a speed (V2) faster than V1.

The matching oil in the vicinity of the holding plate 17 flows toward an end B of the seal member 21 relative to the probe unit 16 due to the fluid friction with the holding plate 17. Therefore, even if the probe unit moves with a constant speed, the liquid level decreases to form a space between the probe 19 and the holding plate 17. The volume of the space formed by the decrease of the liquid level is different depending upon the speed of the probe unit 16. As the speed is faster, the volume becomes larger. Specifically, in FIG. 5, supposing that the volume of the space formed by the decrease of the liquid level at the speed V1 is defined as A1, and the volume of the space formed by the decrease of the liquid level at the speed V2 is defined as A2, A1<A2 is established, so that the appropriate supply amount of the matching oil is different depending upon the speed. Some of the matching oil flowing into the vicinity of the end B of the seal member 21 flow upward of the seal member 21, and leak from the opening 45. If there is air between the probe unit 16 and the holding plate 17 after the probe unit 16 moves to the initial position from the end position, the probe unit 16 has to wait until the matching oil is filled for starting again the measurement. In order to avoid this situation, the matching oil is supplied even in the vertical scan for preventing the formation of the space during the scan.

Figure 6:
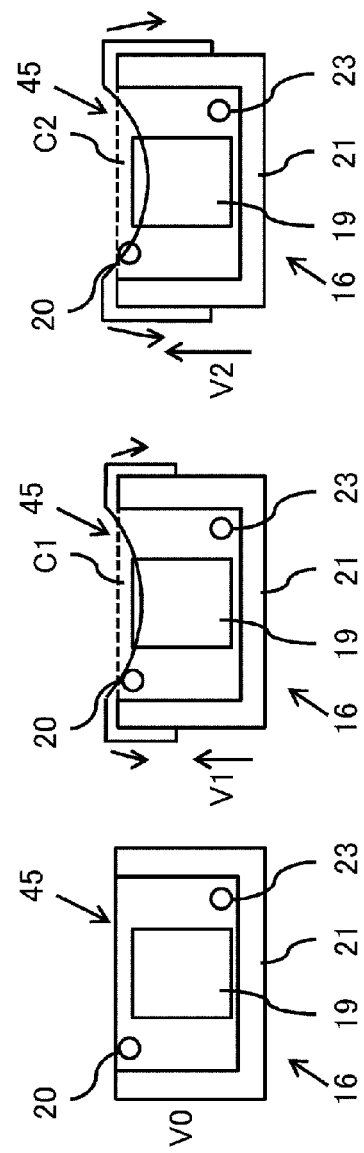
FIGS. 6A to 6C are views illustrating a state of a liquid level during a vertical scan.

FIG. 6 is a schematic view illustrating a state of the matching oil in case where the probe unit 16 scans from bottom up without supplying the matching oil after the matching oil is filled in the space 22. FIG. 6A illustrates the state in which the probe unit 16 stops. FIG. 6B illustrates the state in which the probe unit 16 scans with the constant speed (V1). FIG. 6C illustrates the state in which the probe unit 16 scans with the speed (V2) faster than V1.

Even in this case, the flow is caused in the matching oil due to the fluid friction with the holding plate 17. Because of this flow, the liquid level decreases to form a space between the probe 19 and the holding plate 17, even if the probe unit 16 moves with the constant speed. Even in the upward scan, the volumes C1 and C2 of the spaces formed by the decrease of the liquid level at the speed V1 and at the speed V2 are different from each other. Specifically, the volume C2 corresponding to the higher speed V2 is larger. Accordingly, even in the vertical scan, the appropriate supply amount of the matching oil is different depending upon the speed. In addition, the volume A1 of the space formed when the probe unit 16 moves horizontally with the speed V1 and the volume C1 of the space formed when the probe unit 16 moves vertically with the speed V1 are different. Even when the scan indicated by 47b in FIG. 4 is performed, the probe unit 16 can make measurement without providing a stand-by time after reaching the measurement position. In addition, the volume A1 of the space formed when the probe unit 16 moves horizontally with the speed V1 and the volume C1 of the space formed when the probe unit 16 moves vertically with the speed V1 are different. In other words, the volume of the space formed by the decrease of the liquid level is different depending upon the scanning direction, i.e., in the horizontal direction or vertical direction, and upon the speed. Therefore, the appropriate supply amount of the matching oil is different.

In order to supply the matching oil in different amount, the control unit 100 has a supply-amount pattern of the matching oil according to the speed when the probe unit 16 moves in the horizontal direction, and a supply-amount pattern of the matching oil according to the speed when the probe unit 16 scans in the vertical direction. The supply-amount pattern may be provided by a table or numerical data retained in a memory or other memory medium.

Figure 7:
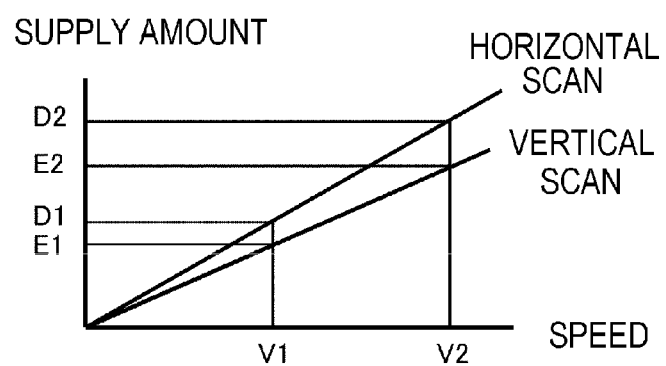
FIG. 7 is a graph illustrating a supply-amount pattern according to the embodiment 1.

FIG. 7 is a graph illustrating the supply-amount pattern. This graph illustrates the relationship between the scanning speed (abscissa axis) and the supply amount (ordinate axis) by which the matching oil between the holding plate 17 and the probe unit 16 can be retained when the probe unit 16 scans with this scanning speed. The supply-amount pattern calculated from the viscosity of the matching oil or the shape of the space 22 formed by the seal member 21, or the supply-amount pattern optimized by the actual measurement is recorded to the control unit 100. This graph is only illustrative, and the present invention is not limited thereto. The scanning speed is based upon the process of the control unit 100 for scanning the probe unit 16. However, a speed sensor may be provided, and the supply amount may be controlled according to the speed sensed by the speed sensor.

When the speed of the arrow 47a in FIG. 4 is V2, the matching oil in an amount of D2 is supplied based upon the supply-amount pattern for the horizontal scan in FIG. 7. If the speed for the vertical scan for moving the probe unit 16 from the end position to the initial position is V2, the matching oil is supplied in an amount of E2. When the viscosity of the matching oil is high, and the influence caused by the acceleration is small, the matching oil may be supplied in the supply amount according to the speed change even in the acceleration/deceleration period until the probe unit 16 reaches the speed V2. Specifically, the supply amount with the speed V1 in a certain period becomes D1. When the probe unit makes an oblique scan as indicated by the arrow 47b in FIG. 4, which means the horizontal scan and the vertical scan are simultaneously executed, the supply amount is obtained by the calculation for obtaining the sum of the supply amount with the speed in the horizontal scan and the supply amount with the speed in the vertical scan. The oblique direction corresponds to a third direction in the present invention.

Figure 8:
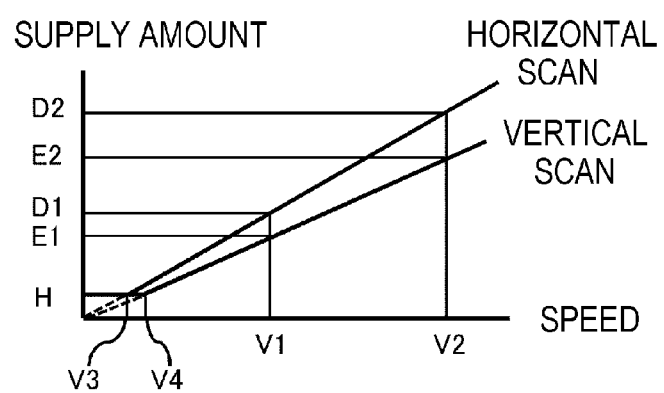
FIG. 8 is another graph illustrating a supply-amount pattern according to the embodiment 1.

FIG. 8 is a view illustrating a supply-amount pattern for supplying the matching oil in a supply amount H even if the probe unit 16 stops. As illustrated in the figure, the supply amount is uniformly set as H when the speed in the horizontal scan is not more than a speed V3, and when the speed in the vertical scan is not more than a speed V4. With this control, the supply amount H is secured even if the probe unit stops or the scanning speed is slow such as not mo re than a predetermined value. Therefore, the matching oil can be overflown, whereby the mixture of foreign matters can be reduced, and the air bubbles can be removed. Here, the range where the supply amount is not more than the predetermined value H in the supply-amount pattern in FIG. 7 is set as the uniform supply amount for both the horizontal scan and the vertical scan. However, a predetermined value may be determined for each of the supply-amount patterns.

With this control, the matching oil can always be filled between the holding plate 17 and the probe unit 16 for any one of the horizontal scan, the vertical scan, and the oblique scan. Since the value used for the process by the control unit 100 is used as the scanning speed, the drive of the pump 25 can be controlled before the scanning speed is changed. Accordingly, the matching oil is supplied before the liquid level is decreased, whereby the matching oil can more surely be filled. The scanning speed can be set in consideration of a time difference from the start of the control by the control unit 100 till the matching oil is supplied by the drive of the pump 25. In the present embodiment, the supply-amount pattern in the horizontal direction and the supply-amount pattern in the vertical direction are set. However, the supply-amount patterns may be set in detail for the right direction, left direction, upward direction and downward direction.

When there is one supply-amount pattern, the supply amount corresponding to the case where the volume of the space between the probe 19 and the holding plate 17 is larger is used. For example, when the relationship of the supply amount based upon the scanning direction and the speed is as illustrated in FIG. 7, the supply-amount pattern for the horizontal scan is also applied to the vertical scan. Specifically, when the probe unit makes a vertical scan with the speed V1, the supply amount of E1 is enough, but actually, the matching oil in the supply amount of D1 is supplied. The matching oil in the amount of D1-E1 that is the difference in the supply amount is leaked from the opening 45 on the top of the probe unit 16.

On the other hand, when the supply amount of the matching oil is controlled according to the scanning direction and the speed as in the present embodiment, the amount of the matching oil leaked from the probe unit 16 can be reduced. Therefore, the contamination of the inside of the apparatus due to the scatter of the leaked matching oil is reduced, resulting in that the maintenance can be facilitated. Since the scatter of the matching oil is reduced, the collecting efficiency of the matching oil is enhanced. The apparatus needs less replenishment of the matching oil, thus economical.

<Embodiment 2>

Figure 9:
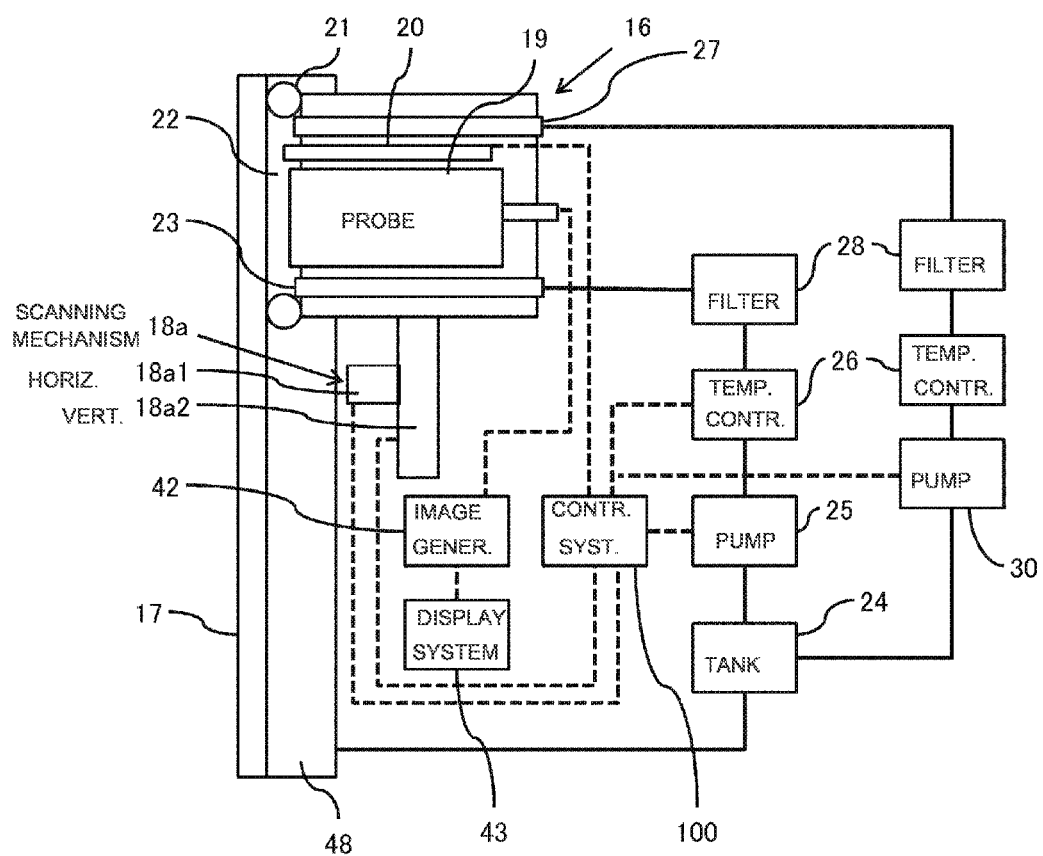
FIG. 9 is a view illustrating a schematic configuration of a photoacoustic apparatus according to an embodiment 2.

FIG. 9 is a view illustrating a schematic configuration of a photoacoustic apparatus according to an embodiment 2. In the embodiment 2, a supply port 27 is provided on a position opposite to the probe unit 16 across the probe 19, in addition to the supply port 23. When the matching oil is supplied to the supply port 27, a pump 30 is driven.

Figure 10:
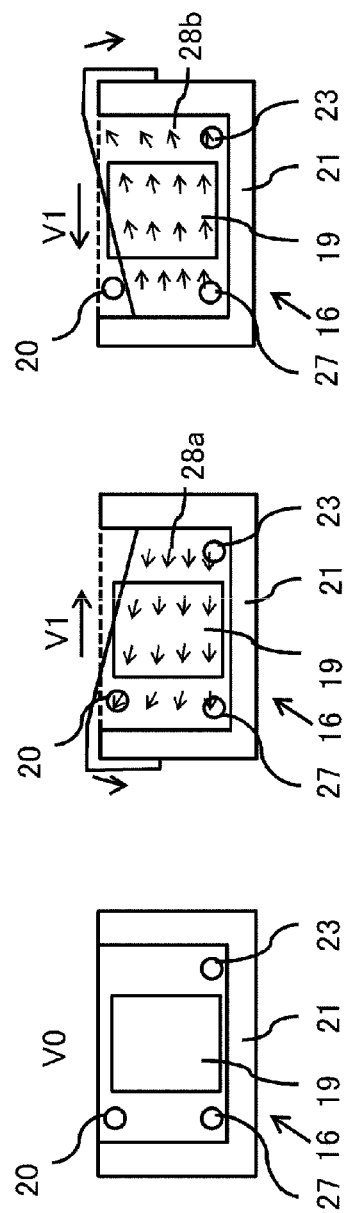
FIGS. 10A to 10C are views illustrating a state of a liquid level depending upon the difference in the scanning direction during a horizontal scan.

FIG. 10 is a view illustrating the probe unit 16 and a state of the liquid level. FIG. 10 illustrates the schematic view of the state of the matching oil when the probe unit 16 makes the horizontal scan without the supply of the matching oil after the matching oil is filled in the space 22. FIG. 10A is a view illustrating the liquid level when the probe unit 16 stops. FIG. 10B is a view illustrating the liquid level when the probe unit 16 makes the scan in the direction of a right arrow. Plural arrows 28a briefly illustrate the relative flow of the matching oil to the probe unit 16 generated by the fluid friction with the holding plate 17. FIG. 10C is a view illustrating the liquid level when the probe unit 16 makes the scan in the direction of a left arrow. Plural arrows 28b briefly illustrate the relative flow of the matching oil to the probe unit 16 generated by the fluid friction with the holding plate 17.

In the embodiment 2, when the probe unit 16 moves to the right in the horizontal direction, the control unit 100 drives the pump 25 to supply the matching oil from the supply port 23. On the other hand, when the probe unit 16 moves to the left, the control unit 100 drives the pump 30 to supply the matching oil from the supply port 27. Specifically, the matching oil is supplied from the supply port present forward in the scanning direction of the probe unit 16. The pump 25 and the pump 30 are provided for the respective supply ports. However, only one pump may be provided, and a flow-channel changeover valve may be provided to make a control. In this case, the matching oil in the supply amount by which the probe unit 16 and the holding plate 17 can be filled with the matching oil is supplied according to the moving speed, as in the embodiment 1.

When the probe unit 16 scans in the vertical direction, the matching oil in an amount according to the speed for the vertical scan is supplied from the supply port 23 and the supply port 27. When the graph in FIG. 7 is employed as the supply-amount pattern, and the moving speed is V1, the matching oil is supplied in an amount of E1 that is the sum of the matching oil from the respective supply ports.

As illustrated in FIG. 10B, the matching oil is supplied from the upstream side of the flow 28a generated by the holding plate 17, when the probe unit 16 scans to the right. As illustrated in FIG. 10C, the matching oil is also supplied from the upstream side of the flow 28b generated by the holding plate 17, when the probe unit 16 scans to the left. Since the supply ports 23 and 27 are formed as described above, the matching oil can appropriately be supplied to each space formed on a different position depending upon the difference in the scanning direction. Accordingly, the matching oil leaked from the seal member 21 is reduced. Therefore, the contamination of the inside of the apparatus due to the scatter of the leaked matching oil is reduced, resulting in that the maintenance can be facilitated. Since the scatter of the matching oil is reduced, the collecting efficiency of the matching oil is enhanced. The apparatus needs less replenishment of the matching oil, thus economical.

<Embodiment 3>

Figure 11:
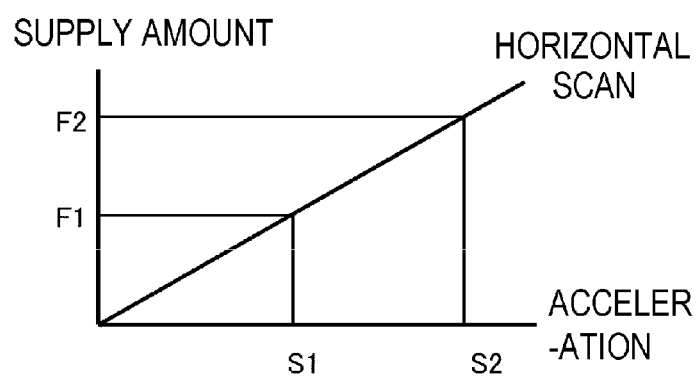
FIG. 11 is a graph illustrating a supply-amount pattern according to acceleration according to an embodiment 3.

FIG. 11 illustrates a supply-amount pattern according to the acceleration. The whole matching oil applies force according to the acceleration from the oil seal 21 during the acceleration. Therefore, the behavior of the matching oil during the acceleration is different from the behavior of the flow of the matching oil due to the fluid friction with the holding plate 17 when the probe unit 16 scans with a constant speed. When the viscosity of the matching oil is low, or when the acceleration period is long, the matching oil is susceptible to the force described above. When the space between the probe unit 16 and the holding plate 17 is filled with the matching oil during the acceleration before the measurement with the constant speed after the acceleration or before the measurement after the probe unit 16 decelerates and stops, the next measurement can smoothly be performed.

Figure 12:
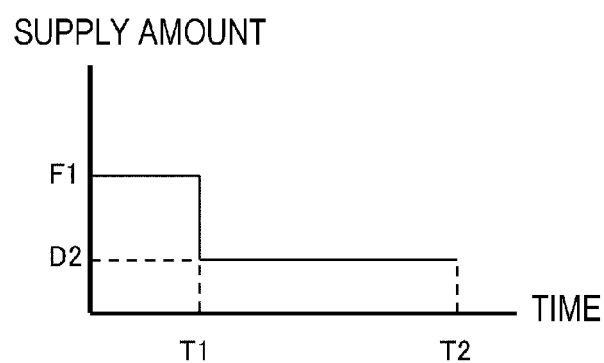
FIG. 12 is a view illustrating a change in the supply amount according to the embodiment 3.

In the present embodiment, the matching oil in the amount according to the space formed by the tilt of the liquid level during the acceleration of the probe unit 16 is supplied. As illustrated in FIG. 11, if the acceleration is S1, the matching oil is supplied in an amount of F1, and if the acceleration is S2, the matching oil in an amount of F2 is supplied during the acceleration. The acceleration obtained by the calculation by the control unit 100 for accelerating the probe unit 16 is employed. An acceleration sensor maybe provided to the probe unit 16, and the acceleration detected by the acceleration sensor may be used. The matching oil may be supplied with the pattern according to the speed in the scan with the constant speed after the acceleration. For example, when the probe unit 16 accelerates with the acceleration S1 to reach the speed V2 in FIG. 7, and then, scans with the constant speed of V2, the matching oil is supplied in the amount of F1 during the accelerated scan, and then, the matching oil is supplied in the amount of D2 in the scan with the constant speed. FIG. 12 illustrates the change in the supply amount in this case. The matching oil is supplied in the amount of F1 before a time T1.

As described above, the supply amount can be increased during the acceleration, while the supply amount can be decreased during the constant speed. Specifically, the matching oil can be supplied in the optimum amount during the acceleration and at the constant speed. When the probe makes the oblique scan by simultaneously making the horizontal scan and the vertical scan as described in the embodiment 1, the matching oil may be supplied in the amount calculated from the supply amount for the horizontal scan and the supply amount for the vertical scan. The present invention can also be applied to the apparatus provided with plural supply ports as in the embodiment 2. Accordingly, the matching oil leaked from the seal member 21 is reduced. Therefore, the contamination of the inside of the apparatus due to the scatter of the leaked matching oil is reduced, resulting in that the maintenance can be facilitated. Since the scatter of the matching oil is reduced, the collecting efficiency of the matching oil is enhanced. The apparatus needs less replenishment of the matching oil, thus economical.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-228945, filed on Oct. 18, 2011, which is hereby incorporated by reference herein its entirety.

What is claimed is:

1. An acoustic wave acquiring apparatus comprising:
a probe configured to receive an acoustic wave from an object via an object holding unit that holds the object;
an acoustic matching material holding unit configured to form a space, which holds an acoustic matching material, between the object holding unit and the probe;
a scanning unit configured to allow the probe to scan in a first direction on a surface of the object holding unit, and in a second direction crossing the first direction; and
a supplying unit configured to supply the acoustic matching material to the space by using a predetermined supply-amount pattern, wherein
the supplying unit uses different supply-amount patterns in the case where the probe scans in the first direction and in the case where the probe scans in the second direction.

2. The acoustic wave acquiring apparatus according to claim 1, wherein
the supply-amount pattern represents a supply amount of the acoustic matching material according to a scanning speed of the probe.

3. The acoustic wave acquiring apparatus according to claim 2, wherein
the supply amount of the acoustic matching material in the supply-amount pattern increases according to an increase in the scanning speed of the probe.

4. The acoustic wave acquiring apparatus according to claim 3, wherein
the supply amount of the acoustic matching material is set uniform when the scanning speed of the probe is not more than a predetermined value in the supply-amount pattern.

5. The acoustic wave acquiring apparatus according to claim 1, wherein
the supply-amount pattern represents the supply amount of the acoustic matching material according to an acceleration of the probe.

6. The acoustic wave acquiring apparatus according to claim 1, wherein
the supply-amount pattern represents a supply amount of the acoustic matching material according to a scanning speed of the probe during when the probe scans with a constant speed, and the supply-amount pattern represents the supply amount of the acoustic matching material according to an acceleration of the probe during when the probe accelerates or decelerates.

7. The acoustic wave acquiring apparatus according to claim 1, wherein
the supplying unit obtains the supply amount of the acoustic matching material from a calculation based upon the supply-amount patterns in the first direction and in the second direction, when the probe scans in a third direction different from the first direction and the second direction.

8. The acoustic wave acquiring apparatus according to claim 1, wherein
the supplying unit has plural supply ports for supplying the acoustic matching material to the space.

9. The acoustic wave acquiring apparatus according to claim 8, wherein
the supplying unit supplies the acoustic matching material to the space from the supply port that is present forward in the scanning direction of the probe.

10. A control method of an acoustic wave acquiring apparatus including a probe that receives an acoustic wave from an object via an object holding unit that holds the object, and an acoustic matching material holding unit that forms a space, which holds an acoustic matching material, between the object holding unit and the probe, the method comprising:
a scanning step in which a scanning unit allows the probe to scan in a first direction on a surface of the object holding unit, and in a second direction crossing the first direction; and
a supplying step in which a supplying unit supplies the acoustic matching material to the space by using a predetermined supply-amount pattern, wherein
different supply-amount patterns are used in the case where the probe scans in the first direction and in the case where the probe scans in the second direction, in the supplying step.

* * * * *